United States Patent
Richardson (10) Patent No.: US 7,905,841 B2
(45) Date of Patent: Mar. 15, 2011

(54) CYTOLOGY DEVICE AND RELATED METHODS OF USE

(75) Inventor: Kevin Richardson, Hopkinton, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 18 days.

(21) Appl. No.: 11/214,826

(22) Filed: Aug. 31, 2005

(65) Prior Publication Data
US 2007/0060839 A1    Mar. 15, 2007

(51) Int. Cl.
A61B 10/00    (2006.01)

(52) U.S. Cl. .......................... 600/562; 600/570

(58) Field of Classification Search ......... 600/562, 600/563, 569, 570, 572; 606/151; 623/1.12, 623/1.2, 1.31, 1.36–1.37, 1.39–1.4
See application file for complete search history.

(56) References Cited

U.S. PATENT DOCUMENTS

| | | | |
|---|---|---|---|
| 2,701,559 A | | 2/1955 | Cooper |
| 4,873,978 A * | 10/1989 | Ginsburg | 606/198 |
| 5,026,377 A * | 6/1991 | Burton et al. | 606/108 |
| 5,192,286 A * | 3/1993 | Phan et al. | 606/127 |
| 5,653,684 A * | 8/1997 | Laptewicz et al. | 604/22 |
| 5,759,187 A * | 6/1998 | Nakao et al. | 606/114 |
| 5,782,840 A | 7/1998 | Nakao | |
| 5,941,869 A * | 8/1999 | Patterson et al. | 604/508 |
| 5,997,547 A | 12/1999 | Nakao et al. | |
| 5,997,557 A * | 12/1999 | Barbut et al. | 606/159 |
| 6,015,429 A * | 1/2000 | Lau et al. | 623/1.2 |
| 6,569,255 B2 * | 5/2003 | Sivacoe | 134/8 |
| 6,695,865 B2 * | 2/2004 | Boyle et al. | 606/200 |
| 6,800,080 B1 * | 10/2004 | Bates | 606/127 |
| 6,814,739 B2 * | 11/2004 | Secrest et al. | 606/114 |
| 7,524,319 B2 * | 4/2009 | Dubrul | 606/113 |
| 2003/0060783 A1 * | 3/2003 | Koole et al. | 604/265 |
| 2003/0144725 A1 * | 7/2003 | Lombardi | 623/1.13 |
| 2004/0267191 A1 * | 12/2004 | Gifford et al. | 604/22 |
| 2005/0255230 A1 * | 11/2005 | Clerc et al. | 427/2.1 |
| 2006/0195118 A1 * | 8/2006 | Richardson | 606/113 |
| 2006/0229645 A1 * | 10/2006 | Bonnette et al. | 606/159 |

OTHER PUBLICATIONS

"WALLSTENT® RX Biliary Endoprosthesis with Permalume® Covering and UNISTEP™ Plus Delivery System"; printed from the website http://www.bostonscientific.com/ on or about Feb. 6, 2004; 5 pages.

"WALLSTENT® RX Biliary Endoprosthesis: Instruction for Use"; printed from the website http://www.bostonscientific.com/ on or about Feb. 6, 2004; 2 pages.

"RX Cytology Brush"; printed from the website http://www.bostonscientific.com/ on or about Feb. 6, 2004; 2 pages.

* cited by examiner

Primary Examiner — Max Hindenburg
Assistant Examiner — Helen Q. Nguyen
(74) Attorney, Agent, or Firm — Finnegan, Henderson, Farabow, Garrett & Dunner LLP (57) ABSTRACT

Embodiments of the invention include a method of obtaining tissue from a body portion. The method includes providing a wire matrix with a covering in a collapsed configuration, advancing the wire matrix through a body lumen to the body portion, expanding the wire matrix, passing at least a portion of the covering against the body portion so as to deposit tissue on the covering, and removing the wire matrix and the covering via the body lumen.

26 Claims, 5 Drawing Sheets

CYTOLOGY DEVICE AND RELATED METHODS OF USE

FIELD OF THE INVENTION

The invention relates to methods and apparatuses for acquiring tissue from a desired body portion. For example, the invention may include a method of acquiring tissue from a desired body portion via an expanding wire matrix having a covering.

BACKGROUND OF THE INVENTION

Taking tissue samples from various parts of the digestive system is often required for analysis. One such system is a bile duct (biliary) system. The biliary system delivers bile produced by the liver to the duodenum where the bile assists other gastric fluids in digesting food. The biliary system includes the liver, as well as a plurality of bodily channels and organs that are disposed between the liver and the duodenum. When the liver produces the bile, the bile enters biliary ducts, having relatively small cross-sectional areas, that are dispersed throughout the liver. These biliary ducts carry the bile away from the liver and gradually merge with other biliary ducts to form larger biliary ducts. The last of the biliary ducts merge into the main biliary duct, from which the bile flows into the duodenum.

The biliary system also includes a gall bladder connected to one or more of the biliary ducts via the cystic duct. The gall bladder stores excess bile produced by the liver and introduces the stored bile into the duodenum via the cystic duct and the biliary ducts when necessary.

Sometimes, however, lesions may grow in portions of the biliary system, for example, one of the biliary ducts, that impede bile from properly flowing through the system. In some cases, the lesions may completely prevent the bile flow. This is undesirable as it interrupts the regular digestive process and may even cause damage to the channels and organs of the biliary system.

In order to properly treat the lesions, it is sometimes necessary to acquire a sample from the lesion, analyze the sample, and then determine a proper treatment based on the analysis. The sample may be acquired by advancing a cytology brush through the gastrointestinal tract to the duodenum, into the biliary system via the main biliary duct, and then up through the bile ducts to the lesion. The cytology brush may then be advanced against the lesion to collect cells for analysis. Certain drawbacks of cytology brushes may include difficulty in steering the brush to the correct location, determining whether the lesion has been brushed, and obtaining sufficient samples for analysis.

SUMMARY OF THE INVENTION

An embodiment of the invention includes a method of obtaining tissue from a body portion. The method includes providing a wire matrix with a covering in a collapsed configuration, advancing the wire matrix through a body lumen to the body portion, expanding the wire matrix, passing at least a portion of the covering against the body portion so as to deposit tissue on the covering, and removing the wire matrix and the covering via the body lumen.

Various embodiments of the invention may include one or more of the following aspects: the wire matrix may define a plurality of spaces between wires of the wire matrix, and the passing step may include depositing tissue on the covering in at least some of the plurality of spaces; providing a catheter containing the wire matrix with the covering in the collapsed configuration; a proximal end of the wire matrix may be connected to a catheter, and a distal end of the wire matrix may be expandable to define an opening; the catheter may be disposed within a sheath and may be configured to longitudinally move relative to the sheath; expanding the wire matrix may include moving the catheter distally relative to the sheath so that the wire matrix self-expands; advancing a guidewire through the body lumen and past the body portion; advancing the wire matrix via the guidewire; the expanded wire matrix may have a proximal end and a distal end; the proximal end may be narrower than the distal end; the passing step may include moving the wire matrix in a proximal direction; tissue deposits on the covering by the wire matrix scraping the tissue from the body portion; the wire matrix may be self-expandable; the expanded wire matrix may have a substantially cone shape.

Another embodiment of the invention includes a method of obtaining tissue from a body portion. The method includes providing a wire matrix with a covering and an open distal end within a sheath, advancing the wire matrix and the sheath through a body lumen to the body portion, removing the sheath from the wire matrix so as to deploy the wire matrix, passing at least a portion of the covering against the body portion so as to deposit tissue on the covering, and removing the wire matrix and the covering via the body lumen.

Various embodiments of the invention may include one or more of the following aspects: the removing step may include moving the sheath proximally relative to the wire matrix; a proximal end of the wire matrix may be connected to a catheter that is coaxially disposed with the sheath; removing the sheath from the wire matrix may permit the wire matrix to expand; the wire matrix may define a plurality of spaces between wires of the wire matrix, and the passing step includes depositing tissue on the covering in at least some of the plurality of spaces; the wire matrix may be provided in a collapsed configuration within the sheath; advancing a guidewire through the body lumen and past the body portion; advancing the wire matrix via the guidewire; the expanded wire matrix may have a proximal end and a distal end; the proximal end may be narrower than the distal end; the passing step may include moving the wire matrix in a proximal direction; tissue may deposit on the covering by the wire matrix scraping the tissue from the body portion; the wire matrix may be self-expandable; the expanded wire matrix may have a substantially cone shape.

A further embodiment of the invention includes a device for acquiring tissue samples. The device may include a catheter, a wire matrix connected to a distal portion of the catheter, the wire matrix having an open distal end, and a covering on at least a part of the matrix. The matrix and covering may be configured to obtain tissue by scraping against a tissue site.

Various embodiments of the invention may include one or more of the following aspects: the wire matrix may be expandable; the wire matrix may be self-expandable; in an expanded configuration, a proximal end of the wire matrix may be narrower than the open distal end; in an expanded configuration, the wire matrix may have a substantially cone shape; the wire matrix may define a plurality of spaces between wires of the wire matrix, and the covering may be configured to receive tissue in at least some of the plurality of spaces; a sheath configured to accommodate the catheter and the wire matrix in a collapsed configuration; a proximal end of the wire matrix may be connected to the catheter; a distal end of the wire matrix may be expandable to define the open distal end; the catheter may be configured to one or both of longitudinally move and rotate relative to the sheath; wires of the wire matrix may include sharp edges configured to assist in obtaining tissue; the covering may cover only a portion of the wire matrix; the covering may cover all of the wire matrix; the distalmost ends of wires of the wire matrix may be unconnected.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

Figure 1A:
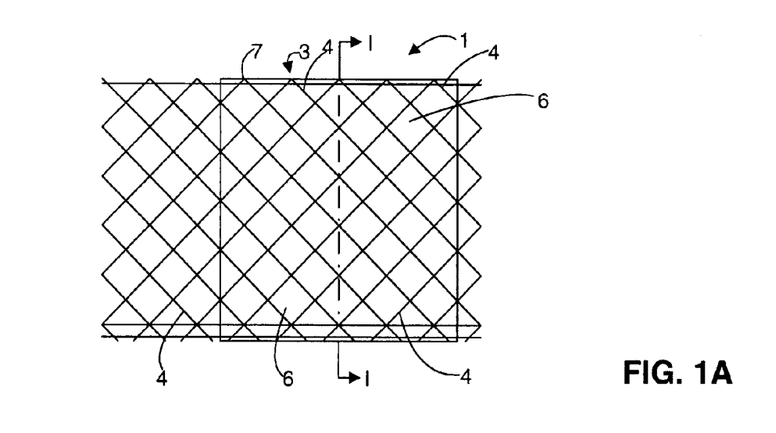
FIG. 1A is a schematic view of a covered stent.
Figure 1B:
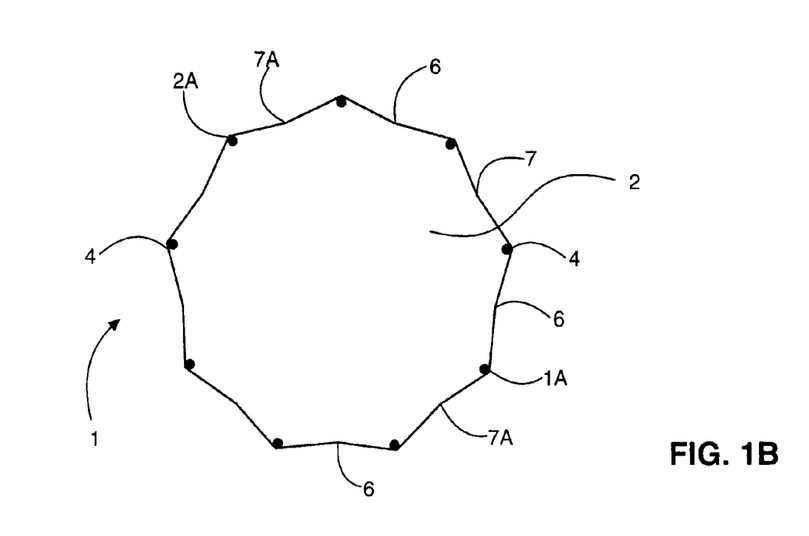
FIG. 1B is a cross-sectional view of the covered stent of FIG. 1A along line I-I of FIG. 1A.

FIGS. 1A-1B depict an exemplary embodiment of a covered stent. The covered stent 1 may have any desired cross-sectional shape and/or configuration. For example, the covered stent 1 may have a substantially circular cross-section. The covered stent 1 may have one or more cross-sectional shapes and/or configurations along its length, and any desired dimensions suitable for deployment in the desired body lumen. For example, the covered stent 1 may have dimensions adapted for placement in a biliary duct having a particular size (e.g., the covered stent 1 may have substantially the same size outer periphery as the inner periphery of the biliary duct having a particular size). The covered stent 1 may be flexible along at least a portion of its length so that it may bend as it is advanced through tortuous body lumens. The covered stent 1 may also be collapsible so that it may be more easily advanced through body lumens in its collapsed state, and self-expandable for deployment through a sheath. The covered stent 1 defines a central lumen 2.

The covered stent 1 includes a matrix 3 manufactured out of any suitable material, for example, one or more metals and/or composites, such as stainless steel or nitinol. In another example, the matrix 3 may be cut from a hypotube through any suitable process, including laser of chemical etching, stamping, etc. The matrix 3 may be composed of a plurality of wires 4 having any desired pattern, configuration, and characteristic suitable for obtaining tissue samples as stent 1 is dragged against the lesion. For example, as shown in FIG. 1A, the wires 4 of the matrix 3 may have a substantially criss-cross configuration.

Figure 4A:
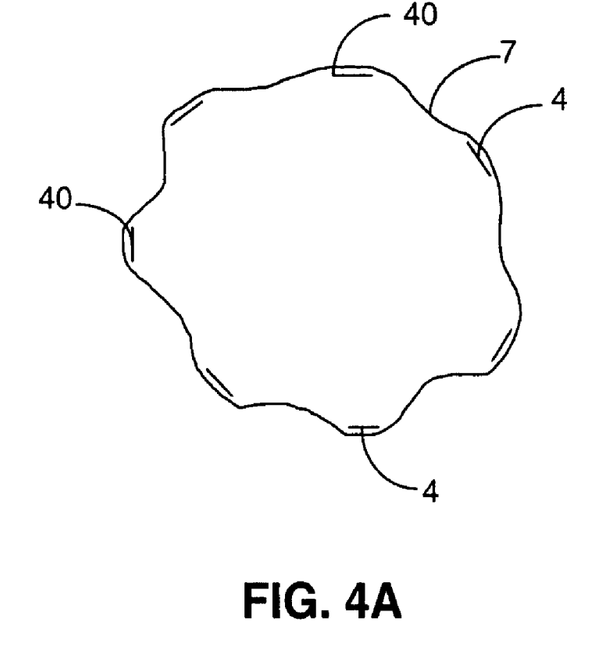
FIG. 4A is a cross-sectional view of a covered stent, according to another embodiment of the invention.
Figure 4B:
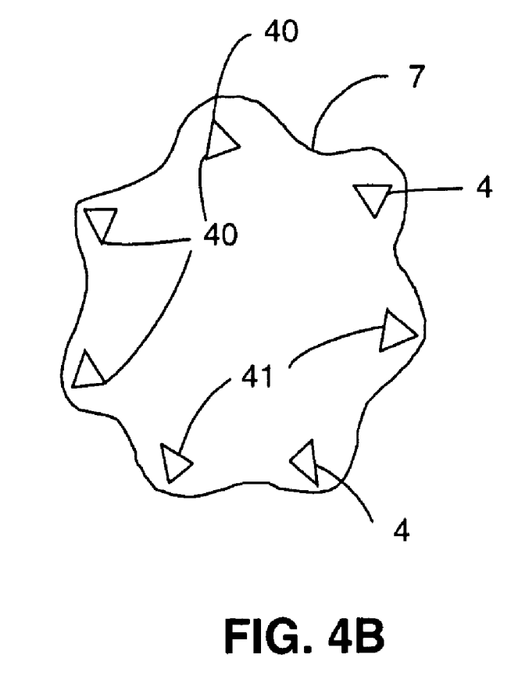
FIG. 4B is a cross-sectional view of a covered stent, according to a further embodiment of the invention.

At least some of the wires 4 may have one or more sharp edges 40 configured to assist in removing tissue. For example, in an alternative embodiment shown in FIG. 4A, wires 4 may be substantially flat having up to two sharp edges 40, or, in a further embodiment shown in FIG. 4B, wires 4 may have a substantially triangular cross-sectional configuration having up to three sharp edges 40. In various embodiments, wires 4 may have number of sharp edges 40 disposed in any suitable configurations. Sharp edges 40 may be formed on wires 4 by any suitable method. These sharp edges 40 may be aligned relative to matrix 3 in any suitable configuration. For example, as shown in FIG. 4A, if the wires 4 are substantially flat, several wires 4 may be disposed so that a flat wire surface faces the longitudinal axis of stent 1 and is substantially perpendicular to a radial line extending from that axis. In another example, as shown in FIG. 4B, if the wires 4 have a substantially triangular cross-sectional shape, one surface 41 of the wires 4 similarly may face the longitudinal axis of stent 1, and the edge 40 opposite the one surface 41 of the wires 4 may point away from the center of stent 1.

The matrix 3 may define a plurality of spaces 6 between the wires 4. The spaces 6 may be of any suitable shape, size, and/or configuration. The spaces 6 may be configured to accommodate and retain tissue. For example, the spaces 6 may be configured to retain tissue within the spaces 6 while at the same time preventing tissue from passing through the spaces 6 into the central lumen 2 of the matrix 3. The spaces 6 provide volume on the covered stent 1 within which tissue deposits.

A covering 7 may cover at least a portion of the matrix 3. The covering 7 may cover all of matrix 3 or leave proximal and/or distal portions of matrix 3 uncovered. The covering 7 may only cover several spaces 6 or portions of spaces 6 on any portion of matrix 3. Selective covering of matrix 3 forms spaces that sample and/or retain tissue. The covering 7 may be made out of any suitable material, for example, a polymer such as PERMALUME™. The covering 7 may be configured to allow cells or other body tissue to become disposed and/or lodged on the surface of the covering 7, for example, by being made of a suitable material or having a suitable coating. In certain embodiments, portions 7A of the covering 7 may be positioned slightly axially inward from an outermost portion 1A of the covered stent 1, for example, the axially outermost portion 1A of the matrix 3. The covering 7 may be comprised of a material suitable for collecting and retaining tissue.

Figure 2A:
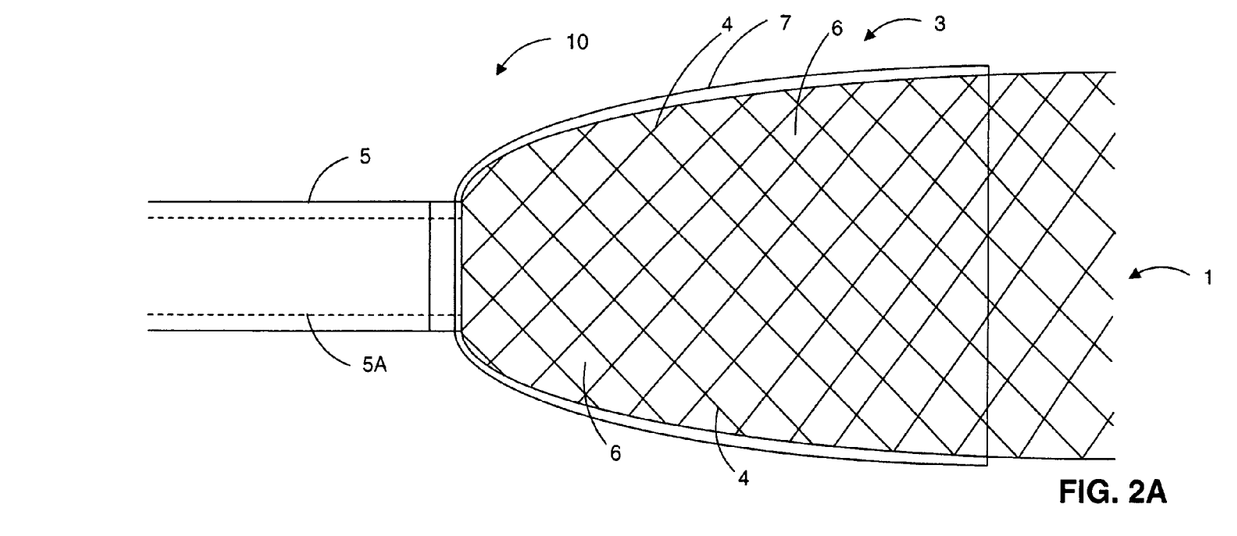
FIG. 2A is a schematic view of a medical device with a covered stent in an expanded configuration, according to an embodiment of the invention.

The stents shown and described herein include an open distal end, as shown in FIG. 2A, for example. The distalmost ends of the wires that comprise the matrix are unconnected and free. A distal end that is open may permit more flexibility for the stent and easier advancement or retraction of the stent within a body lumen.

The stents shown and described in FIGS. 1A, 1B, 4A, and 4B are an exemplary stent that may be used in the method and device of the present invention. Any other suitable stent capable of causing tissue cells to deposit on the stent for removal from the body may be used.

Figure 2B:
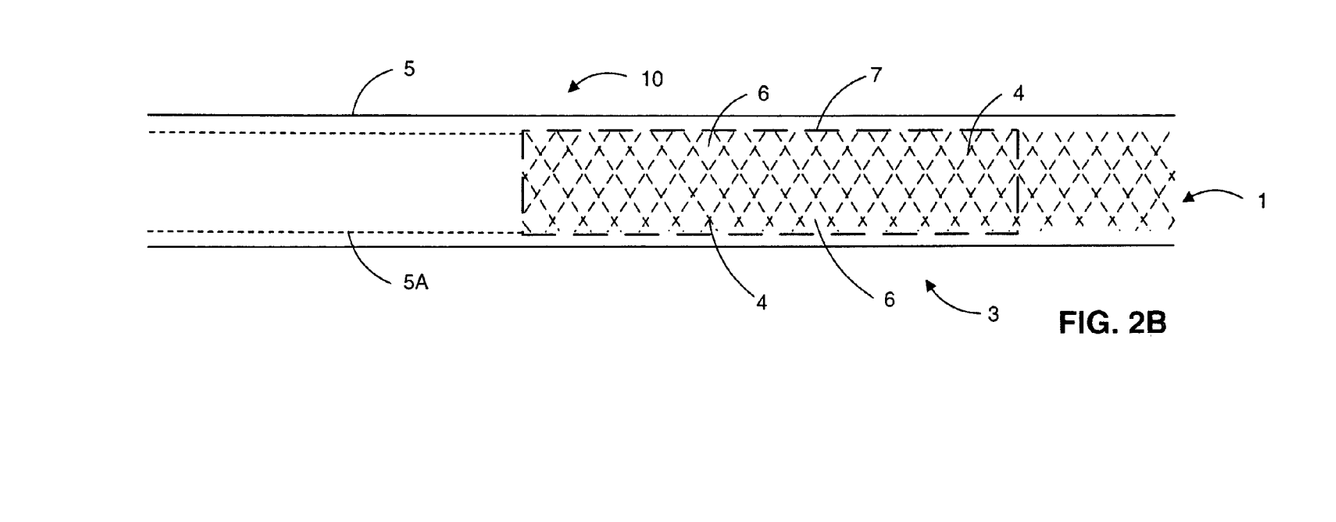
FIG. 2B is a schematic view of the medical device of FIG. 2A with the covered stent in a contracted configuration.

As shown in FIGS. 2A-2B, the stent 1 may be configured to collapse and expand as desired. For example, the stent 1 may be configured to be retracted into a catheter 5 in a collapsed configuration as shown in FIG. 2B and/or advanced out of catheter 5 and at least partially expanded as shown in FIG. 2A. In such an example, the stent 1 may be collapsed and retracted into catheter 5 while the catheter is being advanced through a body lumen to a desired body location. Once the catheter 5 is positioned at the desired body location, the stent 1 may be advanced out of the catheter 5 for expansion.

The covered stent 1 may be retracted into and/or advanced out of the catheter 5 using any method known in the art. For example, the catheter 5 may be a sheath coaxially disposed over a catheter 5A, with catheter 5A being disposed inside catheter 5 and being longitudinally moveable relative to catheter 5. Catheter 5A may also be rotatable relative to catheter 5, for example, to rotate covered stent 1 once it has been deployed in the biliary system 20 so as to assist in acquiring tissue samples. An end of the covered stent 1 may be connected to an end of the catheter 5A through any suitable connection means. Thus, movement of catheter 5A relative to catheter 5 causes the covered stent 1 to move relative to catheter 5, allowing the covered stent 1 to be retracted into and/or advanced out of the catheter 5. Any suitable known handle assemblies may be used at the user end for actuation.

Figure 5A:
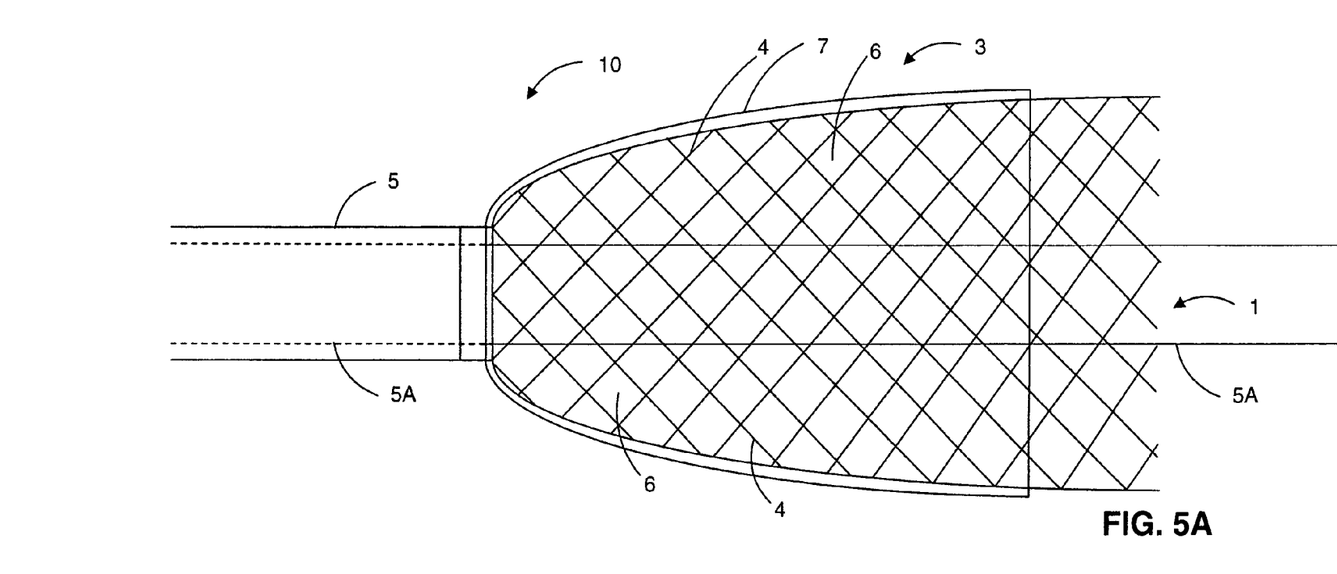
FIG. 5A is a schematic view of a medical device with a covered stent in an expanded configuration, according to yet another embodiment of the invention.
Figure 5B:
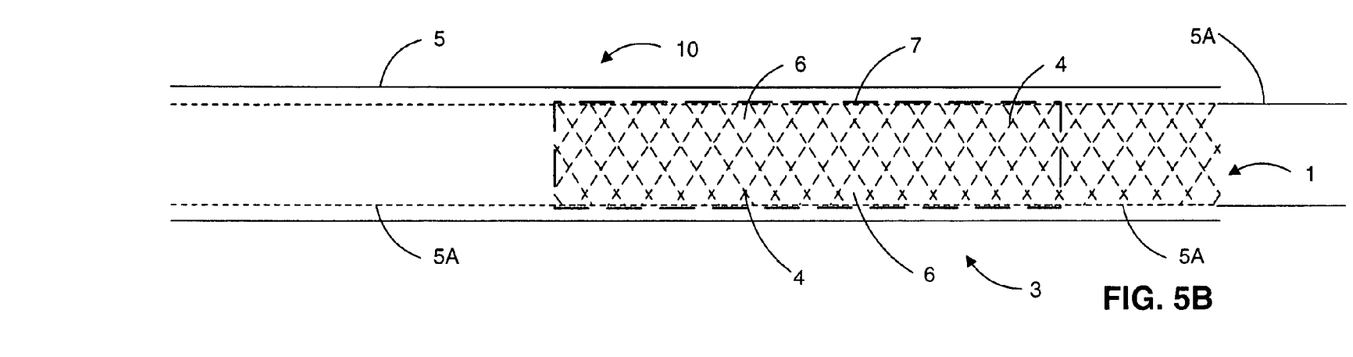
FIG. 5B is a schematic view of the medical device of FIG. 5A with the covered stent in a contracted configuration.

In another embodiment as shown in FIGS. 5A-5B, an end of the covered stent 1 may be connected to a portion of the catheter 5A proximal to the distal end of the catheter 5A through any suitable connection means. The embodiment in FIGS. 5A-5B may operate in substantially the same way as the embodiment in FIGS. 2A-2B. In another alternative, both the proximal and distal ends of the stent 1 may be fixedly connected to catheter 5A. In a still further alternative to the configuration of FIGS. 2A-2B, the distalmost ends of wires 4 may be connected to form a distal tip, and stent 1 would expand much like a urologic basket.

As depicted in FIGS. 3A-3D, embodiments of the invention include methods of using the covered stent 1 to obtain tissue samples. A medical device 10 is provided where the covered stent 1 may be disposed in a catheter 5 in a collapsed state as shown in FIG. 2B. A guidewire 12 may be advanced through a body lumen 20 and past a desired body location. The medical device 10 with the catheter 5 containing the covered stent 1 in a collapsed state may then be advanced through a tortuous body lumen over the guidewire 12 to the desired body location, for example, a portion of the biliary system 20 having one or more lesions 21. The distal end 11 of the medical device 10 may then be advanced past the lesions 21. FIGS. 3A-3D show lesions 21 at opposing sides, or otherwise around the entire periphery, of a body lumen. The method is not limited to use with such lesions and may be used with one or more lesions at various locations and of various size and shape. In the embodiments shown, once the distal end 11 of the medical device 10 is advanced past the lesion 21, the covered stent 1 may be advanced distally out of the catheter 5 so that the distal portion 8 of the covered stent 1 self-expands. When fully deployed, the covered stent 1 may be substantially U-shaped, cone-shaped, and/or have a parabolic configuration due to its fixed connection to catheter 5A at its proximal end 9.

Figure 3A:
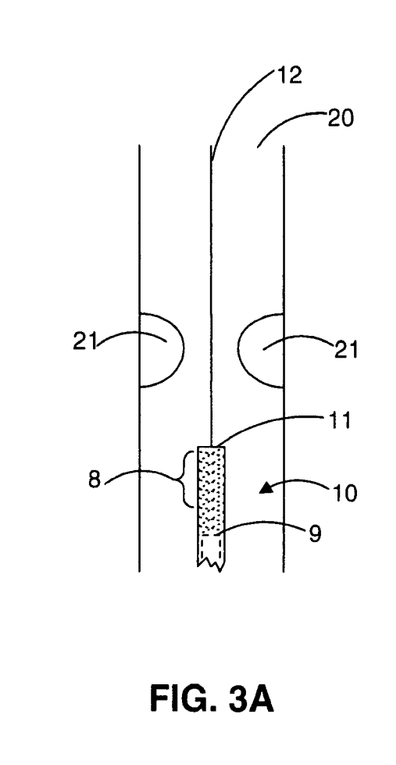
FIGS. 3A-3D are schematic views of steps in a method of using the medical device of FIG. 2A, according to an embodiment of the invention.
Figure 3B:
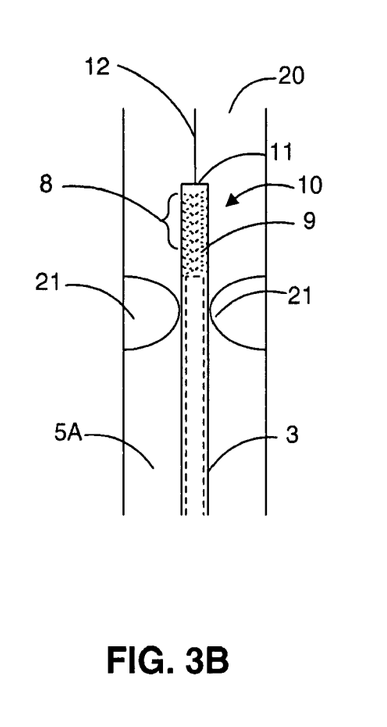
Figure 3C:
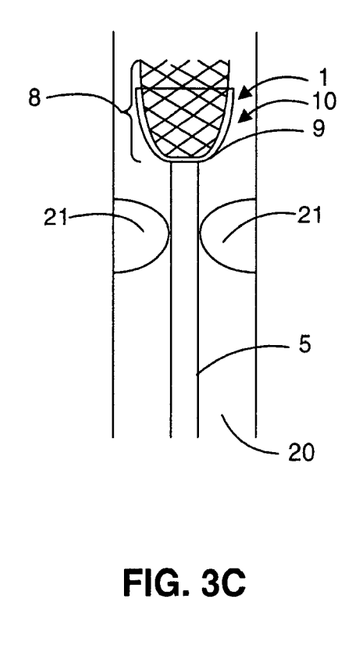
Figure 3D:
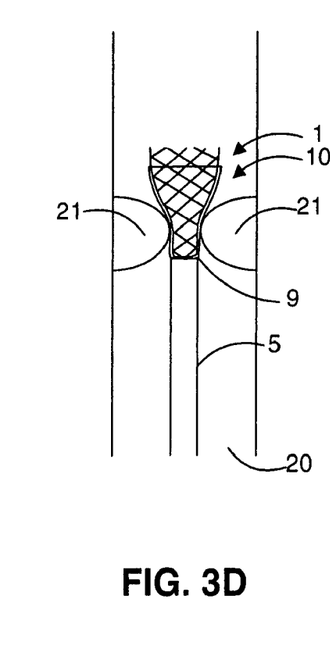

The proximal end 9 of the covered stent 1 may still be in a collapsed state and/or still disposed within the catheter 5, and may be the narrowest portion of the covered stent 1. Once the covered stent 1 is in the deployed state, the covered stent 1 may be moved proximally (along with the inner catheter and outer sheath) such that the outer surface of the covered stent 1 makes contact with portions of the lesions 21 as shown in FIG. 3D. While the covered stent 1 makes contact with portions of the lesion 21, the radial force provided by matrix 3 may scrape, cut, or otherwise remove tissue from the lesion 21 and the removed tissue may become disposed in the spaces 6 on the covering 7. Once the deployed covered stent 1 has been completely advanced proximally past the lesion 21, the covered stent 1 may be collapsed within catheter 5 by moving the inner catheter 5A proximally relative to the outer catheter 5. The device 10 may then be advanced out of the body so that the cells and/or tissue disposed and/or retained by the covered stent 1 may be analyzed. If desired, the medical device 10 and covered stent 1 may be reused with the same patient, for example, by recollapsing the covered stent 1 within the outer catheter 5 and reinserting the device into the body.

In certain embodiments, the medical device 10 with the catheter 5 containing the covered stent 1 in a collapsed state may be advanced through a tortuous body lumen over the guidewire 12 to the desired body location, for example, a portion of the biliary system 20 having one or more lesions 21, substantially as set forth above. According to these other embodiments, the distal end 11 of the medical device 10 is not advanced past the lesion 21 at this time, and instead the covered stent 1, which is currently located proximal to the lesion 21, may be advanced distally out of the catheter 5 so that the distal portion 8 of the covered stent 1 self-expands. Once the covered stent 1 is in the deployed state, the covered stent 1 may be advanced distally such that the outer surface of the covered stent 1 makes contact with portions of the lesions 21 and collects tissue. This may be possible because the covered stent 1, in its fully deployed state, may be sized and configured such that it may still be advanced distally past the lesion. Once the deployed covered stent 1 has been completely advanced distally past the lesion 21, the covered stent 1 may be collapsed within catheter 5 by moving the inner catheter 5A proximally relative to the outer catheter 5. The device 10 may then be advanced out of the body so that the cells and/or tissue disposed and/or retained by the covered stent 1 may be analyzed.

One advantage of using the covered stent 1 to acquire tissue is that by choosing a covered stent 1 with a suitable diameter, the covered stent 1 may be configured to increase the amount of area that the covered stent 1 contacts with the desired body portion, for example, the lesions 21 or the walls of the biliary system 20, so as to increase the quantity of tissue acquired by the covered stent 1. Another advantage is the ability of covered stent 1 to retain tissue inside an outer circumference of covered stent 1, for example, in portions 7A of covering 7 disposed between adjacent wires 4 of matrix 3 or within the lumen of matrix 3 due to the selective covering of matrix 3.

The aforementioned embodiments may be used in any medical or non-medical procedure, including any medical procedure where a tissue sample is desired from any body lumen. In addition, at least certain aspects of the aforementioned embodiments may be combined with other aspects of the embodiments, or removed, without departing from the scope of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for acquiring tissue samples, comprising:
a sheath defining a lumen;

a catheter extending within the lumen of the sheath;
a wire matrix fixedly connected to a distal portion of the catheter, so that the catheter does not extend distally past the wire matrix, wherein the wire matrix and the sheath are moveable relative to each other between a first position and a second position, the first position being an expanded configuration of the wire matrix outside the lumen and the second position being a collapsed configuration of the wire matrix within the lumen, the wire matrix defining a plurality of spaces between wires of the wire matrix; and
a covering on an outer surface of the wire matrix extending from a proximal-most end of the wire matrix to substantially an entire length of the wire matrix, wherein the covering covers substantially all of the plurality of spaces in the wire matrix, and
wherein the device is configured to obtain the tissue samples by scraping an outer surface of the covering against a tissue site, wherein substantially all of the tissue samples obtained by the wire matrix are collected on the outer surface of the covering, and wherein the device does not include any structure disposed within the wire matrix for collapsing the wire matrix.

2. The device of claim 1, wherein the wire matrix is self-expandable.

3. The device of claim 1, wherein in a fully expanded configuration, the wire matrix has a substantially cone shape.

4. The device of claim 1, wherein the proximal-most end of the wire matrix is fixedly connected to the catheter.

5. The device of claim 1, wherein a distal end of the wire matrix is expandable to define an open distal end.

6. The device of claim 5, wherein in a fully expanded configuration, the proximal-most end of the wire matrix is narrower than the open distal end.

7. The device of claim 1, wherein the catheter is configured to longitudinally move relative to the sheath, rotate relative to the sheath, or longitudinally move and rotate relative to the sheath.

8. The device of claim 1, wherein wires of the wire matrix include sharp edges configured to assist in obtaining tissue.

9. The device of claim 1, wherein the covering covers only an outer surface of the wire matrix.

10. The device of claim 1, wherein the wire matrix includes an open distal end.

11. The device of claim 1, wherein distal-most ends of wires of the wire matrix are not directly interconnected by other structure.

12. The device of claim 1, wherein the wire matrix is circumferentially disposed about a longitudinal axis that extends from the proximal-most end of the wire matrix to a distal end of the wire matrix when the wire matrix is in the first position.

13. The device of claim 12, wherein the covering includes a region positioned radially inwards from an outer periphery of the wire matrix.

14. The device of claim 12, wherein the wire matrix has a closed cross-sectional shape along a plane perpendicular to the longitudinal axis.

15. A device for acquiring tissue samples, comprising:
a sheath defining a lumen;
a catheter extending within the lumen of the sheath;
a wire matrix connected to a distal portion of the catheter, so that the catheter does not extend distally past the wire matrix, wherein the wire matrix and the sheath are moveable relative to each other between a first position and a second position, the first position being an expanded configuration of the wire matrix outside the lumen and the second position being a collapsed configuration of the wire matrix within the lumen, the wire matrix defining a plurality of spaces between wires of the wire matrix; and
a covering extending over the wire matrix to cover substantially all of the plurality of spaces of the wire matrix, wherein the device is configured to obtain the tissue samples by scraping an outer surface of the covering against a tissue site to collect substantially all of the obtained tissue on the outer surface of the covering without any of the obtained tissue travelling into the wire matrix through a space of the plurality of spaces, the device being further configured to take the obtained tissue into the lumen of the sheath when the wire matrix retracts into the second position, and wherein the device does not include any structure disposed within the wire matrix for substantially collapsing the wire matrix.

16. The device of claim 15, wherein the covering covers only an outer surface of the wire matrix.

17. The device of claim 15, wherein wires of the wire matrix include sharp edges configured to assist in obtaining tissue.

18. The device of claim 15, wherein the covering includes a region positioned radially inwards from an outer periphery of the wire matrix.

19. A device for acquiring tissue samples, comprising:
a sheath defining a lumen;
a catheter extending within the lumen of the sheath;
a wire matrix connected to a distal portion of the catheter, so that the catheter does not extend distally past the wire matrix, wherein the wire matrix and the sheath are moveable relative to each other between a first position and a second position, the first position being an expanded configuration of the wire matrix outside the lumen and the second position being a collapsed configuration of the wire matrix within the lumen, the wire matrix including wires separated by spaces between the wires; and
a covering extending over substantially an entire length of the wire matrix to cover substantially all the spaces and the wires of the wire matrix,
wherein the device is configured to obtain tissue by scraping an outer surface of the covering against a tissue site to collect substantially all of the obtained tissue on the outer surface of the covering,
wherein wires of the wire matrix include sharp edges configured to assist in obtaining tissue.

20. The device of claim 19, wherein the wire matrix is further configured to take the obtained tissue into the lumen of the sheath when the device retracts into the second position.

21. The device of claim 19, wherein, in the second position, the wire matrix extends from a proximal end to a distal end along a longitudinal axis, and the wire matrix is circumferentially disposed about the longitudinal axis.

22. The device of claim 21, wherein a cross-sectional shape of the wire matrix along a plane perpendicular to the longitudinal axis is substantially circular.

23. The device of claim 22, wherein a diameter of the substantially circular cross-section at a location proximate the distal end is greater than a diameter of the substantially circular cross-sectional shape at a location proximate the proximal end.

24. A device for acquiring tissue samples, comprising:
a sheath defining a lumen;
a catheter extending within the lumen of the sheath;
a wire matrix fixedly connected to a distal portion of the catheter, so that the catheter does not extend distally past the wire matrix, the wire matrix having a plurality of wires separated by spaces between the wires, an open distal end, and an outer periphery, wherein the wire matrix and the sheath are moveable relative to each other between a first position and a second position, the first position being an expanded configuration of the wire matrix outside the lumen and the second position being a collapsed configuration of the wire matrix within the lumen; and a covering on the wire matrix, wherein the covering extends along substantially an entire length of the wire matrix and covers substantially all the spaces between the wires of the wire matrix, the covering including a portion located between two adjacent wires, the portion being positioned radially inward from the two adjacent wires, wherein the device is configured to obtain the tissue samples by scraping an outer surface of the covering against a tissue site to collect substantially all of the obtained tissue on the outer surface of the covering, and wherein the device does not include any structure disposed within the wire matrix for collapsing the wire matrix.

25. The device of claim 24, wherein distal-most ends of the plurality of wires are not directly interconnected by other structure.

26. The device of claim 24, wherein the covering covers only an outer surface of the wire matrix.

* * * * *